(12) United States Patent
Trom et al.

(10) Patent No.: US 6,444,725 B1
(45) Date of Patent: Sep. 3, 2002

(54) COLOR-CHANGING DENTAL COMPOSITIONS

(75) Inventors: Matthew C. Trom, Cottage Grove; Joel D. Oxman, Minneapolis, both of MN (US)

(73) Assignee: 3M Innovative Properties Company, St. Paul, MN (US)

(*) Notice: Subject to any disclaimer, the term of this patent is extended or adjusted under 35 U.S.C. 154(b) by 0 days.

(21) Appl. No.: 09/489,612

(22) Filed: Jan. 21, 2000

(51) Int. Cl.$^7$ .................................................. C08J 3/00
(52) U.S. Cl. ........................... 523/118; 522/25; 522/75; 522/908
(58) Field of Search ............................. 523/118; 522/25, 522/908, 75

(56) References Cited

U.S. PATENT DOCUMENTS

| | | |
|---|---|---|
| 3,066,112 A | 11/1962 | Bowen |
| 3,539,533 A | 11/1970 | Lee et al. |
| 3,629,187 A | 12/1971 | Waller |
| 3,709,866 A | 1/1973 | Waller |
| 3,729,313 A | 4/1973 | Smith |
| 3,741,769 A | 6/1973 | Smith |
| 3,751,399 A | 8/1973 | Lee et al. |
| 3,766,132 A | 10/1973 | Lee et al. |
| 3,808,006 A | 4/1974 | Smith |
| 3,860,556 A | 1/1975 | Taylor |
| 4,002,669 A | 1/1977 | Gross et al. |
| 4,012,840 A | 3/1977 | Takeuchi et al. |
| 4,071,424 A | 1/1978 | Dart et al. |
| 4,115,346 A | 9/1978 | Gross et al. |
| 4,150,012 A | 4/1979 | Joos |
| 4,250,053 A | 2/1981 | Smith |
| 4,259,117 A | 3/1981 | Yamauchi et al. |
| 4,292,029 A | 9/1981 | Craig et al. |
| 4,308,190 A | 12/1981 | Walkowiak et al. |
| 4,327,014 A | 4/1982 | Kawahara et al. |
| 4,379,695 A | 4/1983 | Orlowski et al. |
| 4,387,240 A | 6/1983 | Berg |
| 4,394,403 A | 7/1983 | Smith |
| 4,404,150 A | 9/1983 | Tsunekawa et al. |
| 4,503,169 A | 3/1985 | Randklev |
| 4,642,126 A | 2/1987 | Zador et al. |
| 4,652,274 A | 3/1987 | Boettcher et al. |
| 4,695,251 A | 9/1987 | Randklev |
| 4,737,593 A | 4/1988 | Ellrich et al. |
| 4,772,530 A | 9/1988 | Gottschalk et al. |
| 4,871,786 A | 10/1989 | Aasen et al. |
| 4,874,450 A | 10/1989 | Gottschalk |
| 4,954,414 A | 9/1990 | Adair et al. |
| 5,015,180 A | 5/1991 | Randklev |
| 5,055,372 A | 10/1991 | Shanklin et al. |

(List continued on next page.)

FOREIGN PATENT DOCUMENTS

| | | |
|---|---|---|
| EP | 173 567 | 3/1986 |
| GB | 2310855 | 9/1997 |
| JP | 61-44910 | 3/1986 |
| JP | 11-139920 | 5/1999 |
| WO | WO 95/14716 | 6/1995 |

OTHER PUBLICATIONS

Lee Pharmaceuticals USA, Technical Bulletin No. 9040–950, "Prosthodent® VL–2: Photocuring Crown Base Composite & Restobond™ 3: Dual Dentin–Enamel Bonding Agent," (Apr. 1989).

Product Information from Dental Materials Digest—Dentistry's Premier Information Resource, "Protector, Lee Pharmaceuticals," retrieved on Jun. 30, 1999 from website: www.dentaldigest.com.

Crypsis Product Information Brochure, OREC Corporation (1994).

Primary Examiner—Cephia D. Toomer (57) ABSTRACT

An aesthetic dental sealant comprising a hardenable resin, a hardener, and a colorant, the composition has an initial color prior to exposure to actinic radiation and a final color that is different from the initial color subsequent to the composition being exposed to actinic radiation.

31 Claims, 1 Drawing Sheet

U.S. PATENT DOCUMENTS

| | | |
|---|---|---|
| 5,057,393 A | 10/1991 | Shanklin et al. |
| 5,172,809 A | 12/1992 | Jacobs et al. |
| 5,221,202 A | 6/1993 | James |
| 5,328,363 A | 7/1994 | Chester et al. |
| 5,332,429 A | 7/1994 | Mitra et al. |
| 5,348,154 A | 9/1994 | Jacobs et al. |
| 5,354,199 A | 10/1994 | Jacobs et al. |
| 5,538,129 A | 7/1996 | Chester et al. |
| 5,545,676 A | 8/1996 | Palazzotto et al. |
| 5,552,177 A | 9/1996 | Jacobs et al. |
| 5,583,178 A | 12/1996 | Oxman et al. |
| 5,596,025 A | 1/1997 | Oxman et al. |
| 5,639,802 A | 6/1997 | Neckers et al. |
| 5,698,020 A * | 12/1997 | Salz .................. 106/35 |
| 5,762,192 A | 6/1998 | Jacobs et al. |
| 5,971,754 A | 10/1999 | Sondhi et al. |
| 5,998,495 A | 12/1999 | Oxman et al. |
| 6,085,004 A | 7/2000 | Dower et al. |
| 6,187,833 B1 * | 2/2001 | Oxman et al. ............ 522/15 |

* cited by examiner

COLOR-CHANGING DENTAL COMPOSITIONS

FIELD OF THE INVENTION

The present invention relates broadly to dental materials useful in restorative and preventive dental work. Dental materials of the invention provide hardenable compositions having color-changing capability upon exposure to actinic radiation.

BACKGROUND OF THE INVENTION

Sealants are frequently used to deter dental caries that occur due to accumulation of caries-producing microorganisms in a patient's dentition. The areas in the topography of a dentition that are most desirably treated using a sealant are what are commonly referred to as pits and fissures. Sealants are used to fill pits and fissures to achieve a smooth topography, to avoid microorganism accumulation yet not be detrimental to mastication capability.

U.S. Pat. No. 4,150,012 teaches a dental composition made from a two-part system, where each of the two parts comprise a polymerizable resin and an opaquing filler; however, the first container comprises a catalyst, while the second container comprises an accelerator reactive with the catalyst in the first container.

The dental material is chemically cured (via redox reaction) and provides an opaque dental material when cured.

U.S. Pat. No. 5,583,178 provides a composition for indicating visually a cure point of a hydrosilation-curable composition (e.g., a silicone composition) via a color change. A cure indicating dye is added to the curable composition to provide a visual indication of the extent of the hydrosilation reaction (e.g., extent of the crosslinking reaction).

U.S. Pat. No. 5,596,025 provides a dental impression material whose cure can be monitored visually, comprising: 1) a curable silicone polymer; 2) a crosslinker compound containing silicon-bonded hydrogen groups; 3) a hydrosilation catalyst; and 4) one or more cure-indicating dyes that exhibit a color change in the presence of a silicon-bonded hydrogen compound and a hydrosilation catalyst.

Conventional dental sealants are provided in either a clear composition or a composition comprising titanium dioxide for imparting a white color. Placement of dental sealant material on teeth surfaces is often difficult due to the similarity in color of the composition and the teeth, or the lack of color in the composition. Since it is important that sealant material is placed accurately in or on the desired pits and fissures to achieve the benefit of minimizing bacterial accumulation, it would be very beneficial to provide a composition that initially, is easily seen and discernible from the teeth surface, yet upon curing, can advantageously change to a tooth-like color to closely match that of the tooth surface(s).

SUMMARY

The present invention provides a hardenable dental composition having color-changing capability to aid a practitioner in properly placing desired amounts of composition in and on areas of dentition. Methods of using a color-changing dental composition are also provided.

The compositions of the invention have an initial color prior to exposure to actinic radiation and have a different, final color subsequent to exposure to actinic radiation. The compositions are capable of undergoing a change in color of $\Delta E^*$ greater than about 10.

In one aspect of the invention, the compositions of the invention have a final color that is tooth-like, or matches the color of naturally occurring dentition.

In another aspect of the invention, a dye or a combination of dyes can be used to impart a desired initial color to the composition.

In a further aspect of the invention, the compositions and methods of the invention are useful as sealants, restoratives and prostheses.

As used herein the following terms are intended to have the following definitions:

"hardenable" is descriptive of a material that can be cured or solidified e.g., by heating to remove solvent, heating to cause polymerization, chemical cross-linking, radiation-induced polymerization or crosslinking, or the like;

"photo-bleach(able)" means a loss of color upon exposure to actinic radiation;

"hardener" means a system that initiates hardening of a resin, and can be used synonymously with "initiator system."

BRIEF DESCRIPTION OF THE DRAWINGS

The invention will be more fully appreciated by referring to the following non-limiting drawings in which.

DETAILED DESCRIPTION OF THE PREFERRED EMBODIMENTS

The present invention provides a dental material that is capable of changing color upon exposure to actinic radiation. The compositions of the invention can be useful as pit and fissure sealants. Prior to exposing the material to actinic radiation, the composition possesses an initial color that contrasts that of natural teeth. This initial color provides a visual aid so that a practitioner can easily place the composition in precise locations on the tooth surface(s) and in accurate amounts.

Advantageously, the materials of the present invention possess a second color resultant upon exposure of the material to actinic radiation or light, hereinafter referred to as the "final color." The final color of the applied composition preferably closely matches the dentition which surrounds it or alternatively is able to transmit the color of the underlying dentition. By formulating the composition of the invention so that it results in a tooth-like shade and color, the composition can form an "aesthetic" layer upon the tooth surface. "Aesthetic" as used herein, means a composition that is customarily positioned in a visible location on the dentition (e.g., the tops of molars, labial surfaces of incisors and cuspids) and is either visible due to the layer being the outermost layer or can be seen through any overlying layer. As used herein, "tooth-like" color refers to the broad range of colors and shades of naturally occurring teeth, which can be quantified for example, using the Vita™-shade system (covering the range A1 through D4), a tooth color/shade guide frequently used by dental practitioners. Dental materials that match normal tooth color and shades (i.e. tooth-like) are often considered to have high aesthetic quality, especially when the dental material is indistinguishable from the normal tooth surface when viewed from only a short distance.

Alternatively, the composition of the invention can be formulated to provide a final color that provides decorative or cosmetic value. For example, for cosmetic purposes, it may be desirable for the composition to have a specific color other than white or cream (i.e. tooth-like color or shade) so that a visible design or image can be applied to a tooth surface.

A further advantage of the present invention is convenient use of a dental material, where the convenience is based on the quick curing of the compositions. A practitioner can easily cure the compositions of the present invention with the use of a conventional dental curing light.

The dental material of the invention comprises a hardenable resin and a colorant. The colorant may be a dye or may come in the form of a sensitizer, which is a component of an initiator system. Thus, a sensitizer may serve a dual purpose of providing photoactivation to the composition as well as imparting a color to the composition. A preferred initiator system comprises a sensitizer (which may or may not impart color) and an electron donor. Optionally the initiator system may further comprise an onium salt, thus making the initiator system a ternary system.

The dental material of the present invention is preferably provided in the form of a colored composition, where the initial color (before actinic radiation exposure) contrasts that of natural teeth. Coloration of the material is imparted by a colorant. Preferably, the colorant is a dye or a combination of dyes. Alternatively, the color of the composition is achieved by addition of a dye or the combination of a dye and an initiator system.

A dye may be a pigment and therefore includes any types of suitable pigments. The colorants should be added in an effective amount to achieve a desired color for the composition. For health reasons, food, drug and cosmetic grade dyes are preferred. Preferably, at least one of the dyes in the composition of the invention is reactive or a photo-bleachable dye, in order for the final color to be distinguishable from the initial color. Additional dyes which may or may not be reactive or photo-bleachable may be used to achieve a desired color. Thus, a non-reactive dye may impart a certain color or shade when mixed with a reactive dye to achieve a desired initial color of the dental material.

The color formation and bleaching characteristics of the photo-bleachable dye varies depending on a variety of factors such as acid strength, dielectric constant, polarity, amount of oxygen, moisture content in the atmosphere, etc., but the bleaching properties of the dye can be easily determined by irradiating the composition (hardenable resin and colorant) for use and evaluating the change in color. Preferably at least one colorant is at least partially soluble in the resin of the composition.

Suitable colorants that can impart color to the composition of the invention include, for example, methylene blue, amaranth, erythrocin, floxine, rose bengal, acid red, Tartrazine, Sunset Yellow FCF, Fast Green FCF, Brilliant Blue FCF, indigo carmine, phenolphthalain, sulfophthalain, Yale Violet, methyl orange, fluorescene, methyl viologene, indophenol, dimurosbetaine, bromeosin Y, laudamine B, thionine, neutral red, toluidine blue O, indocyanine green, sulfobromophthalain, uranin, lithol rubin B, lake red C, lithol red, tetrachlorotetrabrom fluorescene, brilliant lake red R, deep maroon, toluidine red, tetrabrom fluorescene, fast acid magenta, permanent red, dibromfluorescene, permanent orange, uranine, quinone yellow, WS, alizarin cyanine green F, quinizarine green SS, light green SF yellow, patent blue NA, carbathrene blue, resorcinol brown, alizarin purple SS, brilliant fast scarlet, permanent red F5R, Ponceaux SX, fast red S, oil orange SS, poral yellow 5G, fast light yellow 3G, naphthol green B, Ginea Green B, Sudan Blue B, alizarol purple, naphthol blue black, crocin, crocin blue, orange paprica, chlorophyl, cartamine, safflower yellow, beet red, direct fast yellow GC, direct fast orange, direct fast scarlet 4BS, fast red 6BLL, direct sky blue SB, direct fast turquoise blue GL, direct copper blue 2B, coprantine green G, direct fast black D, milling yellow O, acid brilliant scarlet 3R, acid violet 5B, azaline direct blue A2G, acid cyanine 6B, acid cyanine 5R, acid cyanine green G, milling brown 3G, acid fast black VLG, acid black WA, cation yellow 3G, cation golden yellow GL, cation flavin 10G, cation yellow 5GL, cation orange R, cation brown 3GL, cation pin FG, cation brilliant red 4G, cation red GTL, cation red BLH, cation red 6B, cation red SB, cation blue GLH, cation navy blue RHL, alizarine, chrome fast blue MB, chrome fast brown KE, chrome black P2B, chrome black T, fast scarlet G base, naphthol AS, naphthol AS-G, vat yellow GCN, vat orange RRTS, indigo, vat blue RSN, vat blue BC, vat brilliant green FFB, vat olive green B, vat olive T, vat brown R, vat gray M, disperse fast yellow G, disperse pink RF, disperse blue FFR, disperse blue green B, disperse yellow 5G, disperse golden yellow GG, disperse yellow RL, disperse yellow 3G, disperse orange B, disperse yellow brown 2R, disperse fast ruby 3B, disperse fast red FB, disperse red FL, disperse red GFL, disperse brilliant pink REL, disperse violet HFRL, disperse blue FB, disperse turquoise blue GL, disperse navy blue 2GL, disperse developer, fluorescent brightener WG, fluorescent brightener ERN, fluorescent brightener AT, fluorescent brighter SA, solvent orange G, solvent fast yellow 3RE, solvent fast red B, solvent fast blue HFL, reactive yellow 3G, reactive orange 2R, reactive red 3B, reactive scarlet 2G, reactive blue 3G, reactive blue R, reactive blue BR, reactive turquoise GF, reactive brilliant blue R, reactive black B, fast yellow G, fast yellow 10G, disazo yellow AAA, disazo yellow AAMX, flavane yellow, chromophthal yellow GR, methine yellow GR, methine yellow, sunset yellow lake, anthrapyrimidine yellow, isoindolinone yellow R, quinophthalone yellow, dinitroaniline orange, pyrazolone orange, dianidine orange, persian orange lake, benzimidazolone orange HL, perynone orange, pyranthrone orange, parared, naphthol red FRR, toluidine red, naphthol carmine FB, naphthol red M, naphthol red BS, naphthol red RN, pyrazolone red, permanent red 2B, lithol red, bon lake red C, lake red C, brilliant carmin 6B, brilliant carmin 3B, Bordeaux 10B, von maroon M, brilliant scarlet G, rhodamine 6G lake, mudder lake, thioindigo Bordeaux, naphthol red FGR, brilliant carmin BS, quinacridone magenta, perylene vermillian, naphthol carmin FBB, perylene red BL, chromophthal scarlet, anthrone red, naphthol red F5RK, erythrocin lake, dianthraquinolyl red, perylene red, perylene maroon, benzimidazolone carmin HF4C, perylene scarlet, amaranth lake, quinacridone red E, pyranthron red, rhodamine B lake, methyl violet lake, alizarine maroon lake, quinacridone red, dioxadine violet, thioindigo magenta, Victoria blue lake, Victoria blue 6G lake, phthalocyanine blue, alkali blue G, indanthrone blue, brilliant green lake, malachite green lake, phthalocyanine green, pigment green B, phthalocyanine green 6Y, benzimidazolone brown HFR, aniline black, dialilide yellow H10G, dialilide yellow HR, carbazole violet, metacresol purple, bromophenol blue, crystal violet, gentiana violet, bromocresol green, bromothimol blue, etc. can be mentioned.

Particularly preferred dyes include Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein and blends thereof. The color of the compositions of the present invention may be additionally imparted by a sensitizing compound.

The color change in the compositions of the invention is initiated by light. Preferably the composition's color change is initiated using actinic radiation, using for example, a dental curing light which emits visible or near infrared (IR) light. The mechanism that initiates the color change in the compositions of the invention may be separate from or substantially simultaneous with the curing mechanism which hardens the resin. Thus, for example, a composition may cure (harden) when polymerization is initiated chemically (redox) or thermally, and the color change from an initial color to a final color may occur subsequent to the hardening process upon exposure to actinic radiation.

The compositions of the invention undergo a color change from an initial color to a second color upon exposing the composition to a source of actinic radiation for a sufficient time to effect color change in the composition. The initial and final colors are different from each other. Preferably, the initial color is one that is easily detected by the unaided human eye to confirm proper placement of the composition on the dentition surface. It is also preferred that the final color have a naturally occurring dentition shade so as to closely match the surrounding environment or be sufficiently clear so as to transmit the color of the underlying dentition. A "naturally occurring dentition shade" can be one that corresponds to the well known alpha-numeric Vita™-shade color designation system or other shade system for characterizing dentition shades.

More quantitatively, the change in color of the composition of the invention from its initial color to a cured color is preferably quantified by a colorimeter test as described in the Test Methods Section below. Using the Color Test, a value of $\Delta E^*$ is determined, which indicates the total color change in a 3-dimensional color space. The human eye can detect a color change of approximately 3 $\Delta E^*$ units in normal lighting conditions. The dental compositions of the present invention are preferably capable of having a color change, $\Delta E^*$, of greater than about 10; more preferably, $\Delta E^*$ is greater than about 15; most preferably $\Delta E^*$ is greater than about 20.

The dental materials of the present invention include a hardenable resin. The resin, in the presence of a hardener, is capable of being hardened to form a polymer network such as, for example, acrylate resins, methacrylate resins, or mixtures thereof. Preferably, the hardenable resin is made from one or more matrix-forming oligomer, monomer, or polymer, or blend thereof.

The hardenable resin should be suitable for use in the oral environment; i.e. non-toxic. Preferably, the dental material is made from an organic resin having sufficient strength and hydrolytic stability.

Examples of suitable resins include acrylate, methacrylate, urethane, and carbamoylisocyanurate resins, e.g., those shown in U.S. Pat. Nos. 3,066,112, 3,539,533, 3,629,187, 3,709,866, 3,751,399, 3,766,132, 3,860,556, 4,002,669, 4,115,346, 4,259,117, 4,292,029, 4,308,190, 4,327,014, 4,379,695, 4,387,240 and 4,404,150, and mixtures and derivatives thereof.

One class of preferred hardenable resins are materials having free radically active functional groups and include monomers, oligomers, and polymers having one or more ethylenically unsaturated groups. Alternatively, the hardenable resin can be a material from the class of resins that include cationically active functional groups. In another alternative, a mixture of hardenable resins that include both cationically curable and free radically curable groups may be used for the dental materials of the invention.

In the class of hardenable resins having free radically active functional groups, suitable materials for use in the invention contain at least one ethylenically unsaturated bond, and are capable of undergoing addition polymerization. Such free radically polymerizable materials include mono-, di- or poly-acrylates and methacrylates such as methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, the diglycidyl methacrylate of bis-phenol A ("Bis-GMA"), bis[1-(2-acryloxy)]-p-ethoxyphenyldimethylmethane, bis[1-(3-acryloxy-2-hydroxy)]-p-propoxyphenyldimethylmethane, and trishydroxyethyl-isocyanurate trimethacrylate; the bis-acrylates and bis-methacrylates of polyethylene glycols of molecular weight 200–500, copolymerizable mixtures of acrylated monomers such as those in U.S. Pat. No. 4,652,274, and acrylated oligomers such as those of U.S. Pat. No. 4,642,126; and vinyl compounds such as styrene, diallyl phthalate, divinyl succinate, divinyl adipate and divinylphthalate. Mixtures of two or more of these free radically polymerizable materials can be used if desired.

For free radical polymerization (curing), an initiation system or hardener can be selected from systems which initiate polymerization via radiation, heat, or redox/autocure chemical reaction. A class of initiators capable of initiating polymerization of free radically active functional groups includes free radical-generating photoinitiators, optionally combined with a photosensitizer or accelerator. Such initiators typically can be capable of generating free radicals for addition polymerization upon exposure to light energy having a wavelength between 200 and 1200 nm.

A variety of visible or near-IR photoinitiator systems may be used for photopolymerization of free-radically polymerizable materials useful in the invention. For example, in free radical polymerization (curing), a photoinitiation system can be selected from systems which initiate polymerization via a two component system of an amine and an α-diketone as described in U.S. Pat No. 4,071,424, which is herein incorporated by reference. Alternatively and preferably, the resin can be combined with a three component or ternary photoinitiator system such as described in U.S. Pat No. 5,545,676 which is incorporated herein by reference.

In the ternary photoinitator system, the first component is an iodonium salt, e.g., a diaryliodonium salt. The iodonium salt is preferably soluble in the monomer and shelf-stable (i.e., does not spontaneously promote polymerization) when dissolved therein in the presence of the sensitizer and donor. Accordingly, selection of a particular iodonium salt may depend to some extent upon the particular monomer, polymer or oligomer, sensitizer and donor chosen. Suitable iodonium salts are described in U.S. Pat. Nos. 3,729,313, 3,741,769, 3,808,006, 4,250,053 and 4,394,403, the iodonium salt disclosures of which are incorporated herein by reference. The iodonium salt can be a simple salt (e.g., containing an anion such as $Cl^-$, $Br^-$, $I^-$ or $C_4H_5SO_3^-$) or a metal complex salt (e.g., containing $SbF_5OH^-$ or $AsF_6^-$). Mixtures of iodonium salts can be used if desired. Preferred iodonium salts include diphenyliodonium salts such as diphenyliodonium chloride, diphenyliodonium hexafluorophosphate and diphenyliodonium tetrafluoroborate.

The second component in a ternary photoinitiator system is a sensitizer. The sensitizer desirably is soluble in the monomer, and is capable of light absorption somewhere within the range of wavelengths of greater than 400 to 1200 nanometers, more preferably greater than 400 to 700 nanometers and most preferably greater than 400 to about 600 nanometers. The sensitizer may also be capable of sensitizing 2-methyl-4,6-bis(trichloromethyl)-s-triazine, using the test procedure described in U.S. Pat. No. 3,729,313, which is incorporated herein by reference. Preferably, in addition to passing this test, a sensitizer is also selected based in part upon shelf stability considerations. Accordingly, selection of a particular sensitizer may depend to some extent upon the particular monomer, oligomer or polymer, iodonium salt and donor chosen.

A sensitizer may also impart a photobleachable color in addition to the color imparted by the dye or pigment colorant. For example, camphorquinone can impart a yellow color to the materials of the invention and Rose Bengal can impart a reddish color to the materials.

Suitable sensitizers can include compounds in the following categories: ketones, coumarin dyes (e.g., ketocoumarins), xanthene dyes, fluorone acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes and pyridinium dyes. Xanthene dyes include those dyes whose molecular structure is related to xanthene and have a Color Index number ranging from 45000–45999. Ketones (e.g., monoketones or alpha-diketones), ketocoumarins, aminoarylketones and p-substituted aminostyryl ketone compounds are preferred sensitizers. For applications requiring high sensitivity, it is preferred to employ a sensitizer containing ajulolidinyl moiety. For applications requiring deep cure (e.g., cure of highly-filled composites), it is preferred to employ sensitizers having an extinction coefficient below about 1000, more preferably below about 100, at the desired wavelength of irradiation for photopolymerization. Alternatively, dyes that exhibit reduction in light absorption or photobleaching at the excitation wavelength upon irradiation can be used.

For example, a preferred class of ketone sensitizers has the formula:

$$ACO(X)_bB$$

where X is CO or $CR^5 R^6$, where $R^5$ and $R^6$ can be the same or different, and can be hydrogen, alkyl, alkaryl or aralkyl, b is zero or one, and A and B can be the same or different and can be substituted (having one or more non-interfering substituents) or unsubstituted aryl, alkyl, alkaryl, or aralkyl groups, or together A and B can form a cyclic structure which can be a substituted or unsubstituted cycloaliphatic, aromatic, heteroaromatic or fused aromatic ring.

Suitable ketones of the above formula include monoketones (b=0) such as 2,2-, 4,4- or 2,4-dihydroxybenzophenone, di-2-pyridyl ketone, di-2-furanyl ketone, di-2-thiophenyl ketone, benzoin, fluorenone, chalcone, Michler's ketone, 2-fluoro-9-fluorenone, 2-chlorothioxanthone, acetophenone, benzophenone, 1- or 2-acetonaphthone, 9-acetylanthracene, 2-, 3- or 9-acetylphenanthrene, 4-acetylbiphenyl, propiophenone, n-butyrophenone, valerophenone, 2-, 3- or 4-acetylpyridine, 3-acetylcoumarin and the like. Suitable diketones include aralkyldiketones such as anthraquinone, phenanthrenequinone, o-, m- and p-diacetylbenzene, 1,3-, 1,4-, 1,5-, 1,6-, 1,7- and 1,8-diacetylnaphthalene, 1,5-, 1,8- and 9,10-diacetylanthracene, and the like. Suitable alpha-diketones (b=1 and X=CO) include 2,3-butanedione, 2,3-pentanedione, 2,3 -hexanedione, 3,4-hexanedione, 2,3-heptanedione, 3,4-heptanedione, 2,3-octanedione, 4,5-octanedione, benzil, 2,2'-3 3'- and 4,4'-dihydroxylbenzil, furil, di-3,3'-indolylethanedione, 2,3-bornanedione (camphorquinone), biacetyl, 1,2-cyclohexanedione, 1,2-naphthaquinone, acenaphthaquinone, and the like.

The third component of a ternary initiator system is a donor. Preferred donors include, for example, amines (including aminoaldehydes and aminosilanes), amides (including phosphoramides), ethers (including thioethers), ureas (including thioureas), ferrocene, sulfinic acids and their salts, salts of ferrocyanide, ascorbic acid and its salts, dithiocarbamic acid and its salts, salts of xanthates, salts of ethylene diamine tetraacetic acid and salts of tetraphenylboronic acid. The donor can be unsubstituted or substituted with one or more non-interfering substituents. Particularly preferred donors contain an electron donor atom such as a nitrogen, oxygen, phosphorus, or sulfur atom, and an abstractable hydrogen atom bonded to a carbon or silicon atom alpha to the electron donor atom. A wide variety of donors is disclosed in U.S. Pat. No. 5,545,676, which is incoporated herein by reference.

Alternatively, free-radical initiators useful in the invention include the class of acylphosphine oxides, as described in European Patent Application No. 173567, U.S. Pat. No. 4,737,593 and United Kingdom Pat No. GB 2,310,855. Such acylphosphine oxides are of the general formula $$(R^9)_2—P(=O)—C(=O)—R^{10}$$

wherein each $R^9$ individually can be a hydrocarbyl group such as alkyl, cycloalkyl, aryl, and aralkyl, any of which can be substituted with a halo-, alkyl- or alkoxy-group, or the two $R^9$ groups can be joined to form a ring along with the phosphorous atom, and wherein $R^{10}$ is a hydrocarbyl group, an S—, O—, or N— containing five- or six-membered heterocyclic group, or a —Z—C(=O)—P(=O)— $(R^9)_2$ group, wherein Z represents a divalent hydrocarbyl group such as alkylene or phenylene having from 2 to 6 carbon atoms.

Preferred acylphosphine oxides useful in the invention are those in which the $R^9$ and $R^{10}$ groups are phenyl or lower alkyl- or lower alkoxy-substituted phenyl. By "lower alkyl" and "lower alkoxy" is meant such groups having from 1 to 4 carbon atoms. Most preferably, the acylphosphine oxide is bis(2,4,6-trimethylbenzoyl)phenyl phosphine oxide (IRGACURE™ 819, Ciba Specialty Chemicals, Tarrytown, N.Y.).

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate. The initiator can be employed in catalytically-effective amounts, such as from about 0:1 to about 5 weight percent, based on the weight of ethylenically-unsaturated compound present, of the acylphosphine oxide plus from about 0.1 to about 5 weight percent, based on the weight of ethylenically-unsaturated compound present, of the tertiary amine.

Commercially-available phosphine oxide photoinitiators capable of free-radical initiation when irradiated at wavelengths of greater than 400 nm to 1200 nm include a 25:75 mixture, by weight, of bis(2,6-dimethoxybenzoyl)-2,4,4-trimethylpentyl phosphine oxide and 2-hydroxy-2-methyl- 1-phenylpropan-1-one (IRGACURE™ 1700, Ciba Specialty Chemicals), 2-benzyl-2-(N,N-dimethylamino)-1-(4-morpholinophenyl)-1-butanone (IRGACURE™ 369, Ciba Specialty Chemicals), bis($\eta^5$-2,4-cyclopentadien-1-yl)-bis (2,6-difluoro-3-(1H-pyrrol-1-yl)phenyl) titanium (IRGACURE™ 784 DC, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR™ 4265, Ciba Specialty Chemicals), and ethyl-2,4,6-trimethylbenzylphenyl phosphinate (LUCIRIN™ LR8893X, BASF Corp., Charlotte, N.C.).

Another free-radical initiator system that can alternatively be used in the dental materials of the invention includes the class of ionic dye—counterion complex initiators comprising a borate anion and a complementary cationic dye.

Borate salt photoinitiators are described, for example, in U.S. Pat. Nos. 4,772,530, 4,954,414, 4,874,450, 5,055,372, and 5,057,393, the disclosures of which are incorporated herein by reference. A borate salt photoinitiator may also employ photobleachable sensitizing colorants.

Borate anions useful in these photointiators generally can be of the formula wherein $R^1$, $R^2$, $R^3$, and $R^4$ independently can be alkyl, aryl, alkaryl, allyl, aralkyl, alkenyl, alkynyl, alicyclic and saturated or unsaturated heterocyclic groups. Preferably, $R^2$, $R^3$, and $R^4$ are aryl groups and more preferably phenyl groups, and $R^1$ is an alkyl group and more preferably a secondary alkyl group.

Cationic counterions can be cationic dyes, quaternary ammonium groups, transition metal coordination complexes, and the like. Cationic dyes useful as counterions can be cationic methine, polymethine, triarylmethine, indoline, thiazine, xanthene, oxazine or acridine dyes. More specifically, the dyes may be cationic cyanine, carbocyanine, hemicyanine, rhodamine, and azomethine dyes. Specific examples of useful cationic dyes include Methylene Blue, Safranine 0, and Malachite Green. Quaternary ammonium groups useful as counterions can be trimethylcetylammonium, cetylpyridinium, and tetramethylammonium. Other organophilic cations can include pyridinium, phosphonium, and sulfonium. Photosensitive transition metal coordination complexes that may be used include complexes of cobalt, ruthenium, osmium, zinc, iron, and iridium with ligands such as pyridine, 2,2'-bipyridine, 4,4'-dimethyl-2,2'-bipyridine, 1,1 0-phenanthroline, 3,4,7,8-tetramethylphenanthroline, 2,4,6-tri(2-pyridyl-s-triazine) and related ligands.

Yet another alternative class of initiators capable of initiating polymerization of free radically active functional groups includes conventional chemical initiator systems such as a combination of a peroxide and an amine. These initiators, which rely upon a thermal redox reaction, are often referred to as "auto-cure initiators." They are typically supplied as two-part systems in which the reactants are stored apart from each other and then combined immediately prior to use.

In a further alternative, heat or thermal energy may be used to initiate the curing, or polymerization, of free radically active groups in the presence of free radical-generating thermal initiators. Examples include peroxides such as, for example, benzoyl peroxide and lauryl peroxide, and azo compounds such as, for example, 2,2-azobis-isobutyronitrile (AIBN). Examples of heat sources suitable for the dental materials of the invention include inductive, convective, and radiant. Thermal sources should be capable of generating temperatures of at least 40° C. to 150° C. under normal conditions or at elevated pressure. This procedure is preferred for initiating polymerization of materials occurring outside of the oral environment.

The initiator compounds are preferably provided in the dental materials of the invention in an amount effective to initiate or enhance the rate of cure of the resin system. Photopolymerizable compositions useful in the invention are prepared by simply admixing, under "safe light" conditions, the components as described above. Suitable inert solvents may be employed if desired when effecting this mixture. Any solvent may be used which does not react appreciably with the components of the inventive compositions. Examples of suitable solvents include acetone, dichloromethane, and acetonitrile. A liquid material to be polymerized may be used as a solvent for another liquid or solid material to be polymerized.

The dental materials of the present invention may optionally comprise additional adjuvants suitable for use in the oral environment, including flavorants, anti-microbials, fragrance, stabilizers, viscosity modifiers, rheology modifiers, fillers and fluoride releasing materials. For example, a fluoride releasing glass may be added to the materials of the invention to provide the benefit of long-term release of fluoride. Fluoroaluminosilicate glasses are suitable for the invention, such as a silanol treated fluoroaluminosilicate glass fillers, as described in U.S. Pat. No. 5,332,429. Organic fluoride sources are also suitable for the invention, such as those described in U.S Pat. No. 4,871,786. Other suitable adjuvants include agents that impart fluorescence and/or opalescence.

Any conventional method of preparing a dental composition may be used to make the dental materials of the present invention. The colorant may be present in the composition in amounts greater than about 0.001 wt % but less than about 1 wt % of the total composition. The amount of colorant may vary depending on the extinction coefficient, the ability of the human eye to discern the initial color, and the desired color change. The colorant and initiator system (i.e. hardener) combined may be present in the composition in an amount between 0.001 wt % and about 10 wt % of the total composition. The resin may be present in the composition in an amount between about 90 wt % and 99.9 wt % of the total composition.

The three components of a photoinitiator system are present in the compositions of the invention in "photochemically effective amounts"; that is, amounts of each component sufficient to enable the monomer to undergo photochemical gelation or curing upon exposure to light of the desired wavelength.

A preferred method of using the dental material of the invention is to dispense a desired amount directly onto a tooth surface or surfaces. Application of the color changing materials of the invention can be performed using fine tipped dental instruments, direct extrusion through a syringe, brushes, or a disposable unit-dose delivery system. Once the composition is placed in the desired area(s) the material can then be exposed to actinic radiation to initiate the change in color of the composition from its initial color to a final color. Hardening or curing of the composition may occur simultaneously with the color change. In a preferred composition that comprises a photoinitator system, the color change and curing can be accomplished using for example, a dental curing light. In alternative composition that are thermally or redox cured, the color change may not occur until exposed to actinic radiation.

Conditioning a tooth surface may enhance adhesion of the color changing composition to the tooth or teeth surface(s).

Preferable the surfaces can be etched or primed prior to applying the composition. Preferably, an etching composition and/or priming composition are used at the locations on the tooth surface which a practitioner desires to place the materials of the present invention. Alternatively or in addition to using an etching composition, an air abrasion system may be used.

The compositions of the invention can be photo-bleached using a variety of methods. It is convenient to employ light sources that emit ultraviolet or visible light such as quartz halogen lamps, tungsten-halogen lamps, mercury lamps, plasma arcs, light emitting diodes and lasers.

Optionally, a clear coat or layer may be applied over the aesthetic layer dental material of the present invention. This may be performed in instances where physical protection of the aesthetic layer. is desired, or when a glossy finish may be desired.

TEST METHODS

Color Testing

Initial and final colors were determined using a Hunter-Lab Ultrascan XE Spectrocolorimeter (Reston, Va.). The spectrocolorimeter is standardized using a Diffuse/8° light trap followed by a Diffuse/8° instrument standard (U3322) (L*: 98.99; a*: −0.29; b*: −0.21). The instrument standard is calibrated by direct comparison to HunterLab Master Transfer Standards which are traceable to NIST (National Institute of Standards and Technology). In this example, a small area view was used with a port size of 0.375" diameter. An uncured sample was placed in a cuvette. The sample measured was a 1 mm thick section in the cuvette.

In examples 1, 2, 4 and 5 a cuvette was made with 1 mm thick clear glass sides and had a 1 mm internal thickness. In example 3 a cuvette was prepared using 0.1 mm thick polyester film without a release agent to enhance adhesion of the cured sample to the cuvette wall.

The uncured sample color was measured against a white background (L*: 94.00; a*: −0.92; b*: −0.27) and a reflectance spectrum and L*a*b* color data (as described in "Principles of Color Technology," Billmeyer & Saltzman, Second Edition, 1981) were generated for each sample. The sample was then photo-cured in the cuvette for 30 seconds using a 3M XL3000 Curing Light (3M Co., St. Paul, Minn.) and the reflectance spectrum and L*a*b* measured again.

The L*a*b* system is based on a 3-dimensional color space with the positive X-axis representing red, the negative X-axis representing green, the positive Y-axis representing yellow, the negative Y-axis representing blue, and the Z-axis going from zero (black) to 100 (white) with the origin at 50. E* is a calculation of total color change in the three color dimensions and is described by the following equation:

$$\Delta E^* = \text{Square root}((L_1^* - L_2^*)^2 + (a_1^* - a_2^*)^2 + (b_1^* - b_2^*)^2) \text{ where subscripts "1" indicates initial state and "2" indicates final state.}$$

The human eye can detect a color change of approximately 3 ΔE* units in normal lighting conditions.

All patents referenced herein are incorporated by reference, unless otherwise noted. The following examples are offered to aid in understanding the invention and are not to be construed as limiting the scope of the invention. Unless otherwise indicated, all parts and percentages are by weight.

EXAMPLES

Example 1

Twenty (20) grams of Samples A and B were prepared by mixing the components at 45° C. for 2 hours while protected from light. The samples were mixed in the weight percentages indicated below in Table 1. Following are abbreviations of the components used.

| | |
|---|---|
| BisGMA | Bisphenol A diglycidylether dimethacrylate |
| TEGDMA | Triethyleneglycol dimethacrylate |
| EDMAB | Ethyl-4-dimethylaminobenzoate |
| CPQ | Camphorquinone |
| DPIHFP | Diphenyliodonium hexafluorophosphate |

TABLE 1

| Sample A: | Sample B: |
|---|---|
| 49.113% BisGMA | 49.413% BisGMA |
| 49.113% TEGDMA | 49.413% TEGDMA |
| 1.000% EDMAB | 1.000% EDMAB |
| 0.170% CPQ | 0.170% CPQ |
| 0.004% Rose Bengal | 0.004% Rose Bengal |
| 0.600% DPIHFP | |

Figure 1:
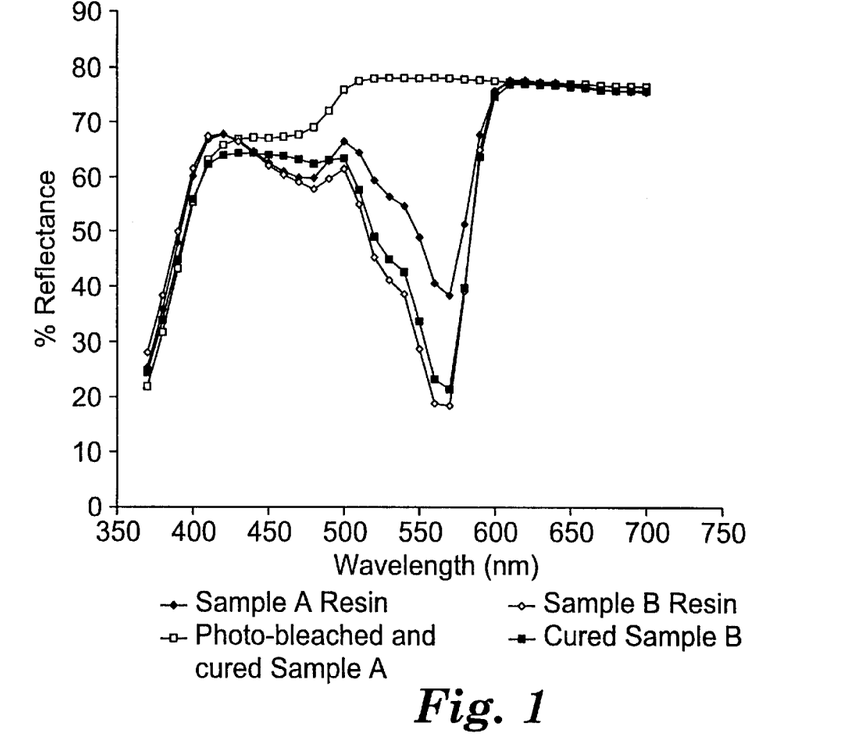
FIG. 1 is a graph depicting color-change in compositions from Example 1.

Referring now to FIG. 1, a plot is shown, of reflectance versus wavelength for Samples A and B described in Example 1, before and after light exposure. The plot indicates the high absorption in the range from 500–600 nanometers for the uncured compositions containing Rose Bengal. Sample A containing diphenyliodonium hexafluorophosphate bleached to give a solid with no red color as indicated by the high reflectance (low absorption) in the 500–600 nanometer region. Sample B that had no iodonium salt had little change in color upon light-cure. The samples were tested for color transmission using the Color Test Procedure described above. Results of the tests are listed in Table 2.

TABLE 2

| | Initial L*a*b* color | Final L*a*b* color | ΔE* |
|---|---|---|---|
| Sample A | 80.86/11.2/−4.56 | 90.19/−2.35/7.56 | 20.4 |
| Comparative Sample B | 74.44/23.71/−14.77 | 75.93/19.37/−13.38 | 4.8 |

Example 2

A light curable composition was prepared with the following formulation wherein the amounts are expressed in parts by weight or weight percent.

| | |
|---|---|
| Bis-GMA | 41.595% |
| TEGDMA | 41.595% |
| CPQ | 0.15% |
| EDMAB | 0.86% |
| DPIHFP | 0.51% |
| Tinuvin P (UV stabilizer) | 0.86% |
| Aerosil R972 (silane treated fumed silica from DeGussa) | 5.13% |
| TiO2 (Silane Treated) | 0.74% |
| Tetrabutylammonium tetrafluoroborate | 8.56% |

The above composition was mixed thoroughly with a high shear mixer for 2 hours at 45° C. yielding a homogeneous white liquid. Four colored formulations were prepared by transferring 0.004 parts of one of four colored dyes shown in the table below to 100 parts of Sample C. Samples were mixed thoroughly with heating to 45° C. yielding visibly colored dental materials. Set out below in Table 3 are the sample numbers, the corresponding dye additive and the observed initial and final color:

TABLE 3

| Composition # | Dye | Initial Color of Compositions | Final Color of Composition after Actinic Radiation |
|---|---|---|---|
| Comparative C1 | None | tooth-like | tooth-like |
| C2 | Rose Bengal | Pink | tooth-like |
| C3 | 4',5'-Dibromo-fluorescein | Pale orange | tooth-like |
| C4 | Methylene Blue | Blue | tooth-like |
| C5 | Eosin Y | Orange/Red | tooth-like |

The above samples were aged at 45° C. for 8 months. L*a*b* color was tested following that period according to the procedure described in Example 1. The initial color was reasonably stable for all dyes evaluated. As shown in Table 4 below, there is some color change of the composition upon curing without additional dye—this was due to the composition having an initial color imparted to it by the sensitizer.

TABLE 4

| Composition # | Initial L*a*b* color | Final L*a*b* color | ΔE* |
|---|---|---|---|
| Comparative C1 | 79.06/−2.41/9.55 | 78.33/−2.26/5.82 | 3.80 |
| C2 | 69.76/12.92/−3.65 | 77.1/−0.58/8.52 | 19.60 |
| C3 | 78.38/3.03/11.11 | 78.63/−2.55/8.04 | 6.37 |
| C4 | 70.05/−17.38/−1.39 | 76.88/−2.24/7.80 | 18.98 |
| C5 | 75.74/14.3/8.18 | 78.14/−2.15/7.34 | 16.65 |

$E^* = \text{Sqrt}((L_1^* - L_2^*)^2 + (a_1^* - a_2^*)^2 + (b_1^* - b_2^*)^2)$

Example 3

A series of six compositions (D1 thru D6) were prepared containing Sample C sealant and varying weight percentages of Rose Bengal. L*a*b* color was tested following that period according to the procedure described in Example 1:

TABLE 5

| Sample # | wt % Rose Bengal | Initial L*a*b* color | Final L*a*b* color | ΔE* |
|---|---|---|---|---|
| D1 | 0.004 | 75.98/26.42/−4.41 | 91.11/−2.56/9.40 | 35.49 |
| D2 | 0.009 | 71.48/35.87/−9.67 | 90.95/−2.43/10.53 | 47.48 |
| D3 | 0.017 | 67.40/43.26/−12.79 | 90.48/−2.11/10.80 | 56.10 |
| D4 | 0.029 | 63.31/48.97/−14.30 | 88.32/0.47/15.20 | 62.03 |
| D5 | 0.057 | 59.02/53.13/−14.34 | 87.28/2.17/17.26 | 66.29 |
| D6 | 0.102 | 55.20/54.62/−12.47 | 78.86/14.26/21.38 | 57.75 |

The ΔE* values were high even at very low levels of dye. The total color change is about the same at high and low dye concentrations due to residual color that does not bleach out at high dye concentrations.

A series of compositions, E1 thru E5, were prepared by combining various amounts of Sample C1 and Sample D1. The resultant compositions contained colorant in varying amounts as listed in Table 6. L*a*b* color was tested following that period according to the procedure described in Example 1:

TABLE 6

| Run # | wt % Rose Bengal | Initial L*a*b* color | Final L*a*b* color | ΔE* |
|---|---|---|---|---|
| E1 | 0.002% | 81.23/15.69/2.97 | 91.42/−2.68/9.19 | 21.91 |
| E2 | 0.0013% | 83.51/11.04/6.02 | 91.57/−2.88/9.55 | 16.47 |
| E3 | 0.0008% | 86.60/5.03/10.74 | 91.59/−2.68/8.32 | 9.50 |
| E4 | 0.00044% | 88.52/2.54/12.20 | 91.99/−2.84/9.11 | 7.11 |
| E5 | 0.0% | 91.22/−3.57/18.18 | 91.84/−2.78/8.37 | 9.86 |

Example 4

A resin composition was prepared which contained:
48.453% BisGMA
48.453% TEGDMA
1.000% EDMAB
0.170% CPQ
1.000% Tinuvin P
0.600% DPIHFP
0.021 Methylene Blue
0.033 Toluidine Blue
0.197 Eosin Y
0.011 Methylene Violet
0.063 Rose Bengal The resin was stirred for 24 hours at 45° C. The resin was a very dark red-brown in color and lightened to a smoky color upon photo-bleaching and curing with a Dental Curing Light for 1 minute. L*a*b* color was tested following that period according to the procedure described in Example 1 and reported in Table 7.

TABLE 7

| Resin | Initial L*a*b* color | Final L*a*b* color | ΔE* |
|---|---|---|---|
| Dark resin | 26.33/3.25/−0.63 | 58.12/32.76/46.10 | 63.76 |

Figure 2:
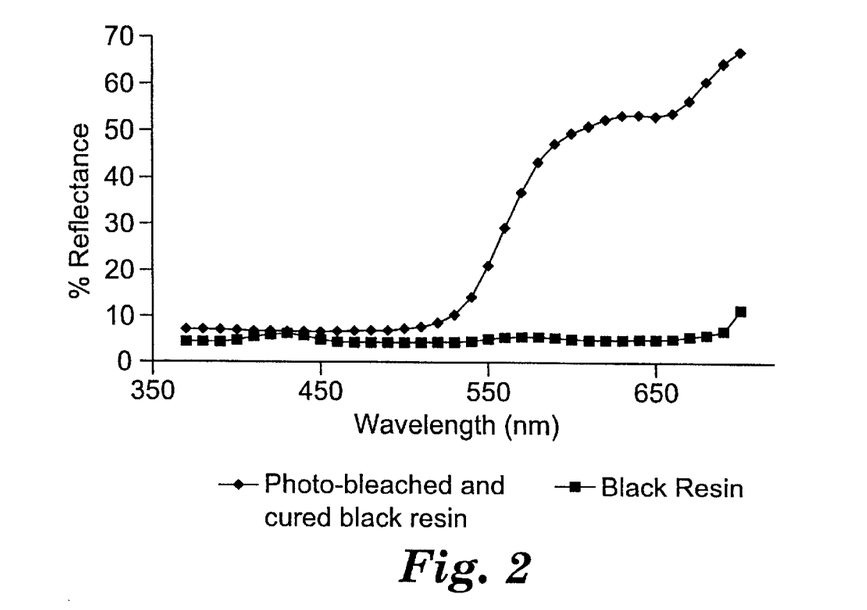
FIG. 2 is a graph depicting color-change in a dark composition in Example 4.

FIG. 2 is a plot of reflectance versus wavelength for the sample described in Example 4 before and after light cure. The plot indicates very low reflectance across the entire spectrum indicating a very dark composition, nearly black in color for the uncured sample. The cured and photo-bleached sample was observed to have bleached significantly as indicated by a much higher reflectance in the 550–700 nm range of the spectrum in the cured resin plot.

Example 5

A two-part resin system was prepared that would allow for chemical and light-cure of a photobleachable system.

| Part A | | Part B | |
|---|---|---|---|
| BisGMA | 49.900% | BisGMA | 49.4% |
| TEGDMA | 49.900% | TEGDMA | 49.4% |
| CPQ | 0.040% | Benzoyl Peroxide | 1.2% |
| Dihydroxyethyl P-toluidine | 0.080% | | |
| Diphenyliodonium hexafluoroantimonate | 0.070% | | |
| Toluidine Blue | 0.002% | | |

Each resin system was mixed thoroughly under safe-light conditions to dissolve all components. The resultant resins were clear and homogenous. The Part A resin was green-blue in color. Part B resin was colorless. Upon 40-second cure with a dental curing light, the Part A composition cured to a hard, colorless solid. When mixed in approximately equal volumes, Parts A and B reacted chemically over a period of about 15 minutes to give a hard, blue-green solid. Upon 40-second exposure with a dental curing light, the solid bleached from blue-green to clear (nearly colorless).

What is claimed:

1. An aesthetic dental sealant comprising a hardenable resin, a hardener, and a photobleachable dye, wherein the hardener comprises a sensitizing compound different from the photobleachable dye, and wherein the dental sealant has an initial color prior to exposure to actinic radiation and a final color that is different from the initial color subsequent to the dental sealant being exposed to actinic radiation.

2. The dental sealant of claim 1 wherein the change in color from the initial color to the final color has a $\Delta E^*$ of greater than about 10.

3. The dental sealant of claim 1 wherein the change in color from the initial color to the final color has a $\Delta E^*$ of greater than about 15.

4. The dental sealant of claim 1 wherein the change in color from the initial color to the final color has a $\Delta E^*$ of greater than about 20.

5. The dental sealant of claim 1 further comprising a fluoride source.

6. The dental sealant of claim 1 further comprising a non-photobleachable dye.

7. The dental sealant of claim 1 wherein the hardener comprises a sensitizing compound, an electron donor, and an iodonium salt.

8. The dental sealant of claim 1 wherein the photobleachable dye is selected from the group consisting of xanthene dyes and fluorone dyes.

9. The dental sealant of claim 1 wherein the photobleachable dye is selected from the group consisting of Rose Bengal, Methylene Violet, Methylene Blue, Fluorescein, Eosin Yellow, Eosin Y, Ethyl Eosin, Eosin bluish, Eosin B, Erythrosin B, Erythosin Yellowish Blend, Toluidine Blue, 4',5'-Dibromofluorescein, and blends thereof.

10. The dental sealant of claim 1 wherein the final color is a tooth-like color.

11. The dental sealant of claim 1 wherein the final color is able to transmit the color of an underlying surface.

12. A method of using an aesthetic dental sealant comprising:

providing a color-changing, dental sealant having an initial color, wherein the dental sealant comprises a hardenable resin, a hardener and a photobleachable dye, with the hardener comprising a sensitizing compound different from the photobleachable dye;

applying the dental sealant onto a tooth surface;

hardening the dental sealant; and exposing the dental sealant to actinic radiation to change the color of the dental sealant from the initial color to a final color.

13. The method according to claim 12 wherein providing, applying, hardening, and exposing are performed sequentially.

14. The method according to claim 12 wherein hardening the dental sealant comprises exposing the dental sealant to actinic radiation.

15. The method according to claim 12 further comprising conditioning a tooth surface, wherein the conditioning is performed prior to applying the dental sealant.

16. The method according to claim 15 wherein the conditioning comprises etching or priming.

17. The method according to claim 15 wherein the conditioning comprises abrading.

18. The method according to claim 12 wherein the dental sealant further comprises a fluoride source.

19. The method according to claim 12 wherein the dental sealant further comprises a non-photobleachable dye.

20. The method according to claim 12 wherein the hardener comprises a sensitizing compound, an electron donor, and an iodonium salt.

21. The method according to claim 12 wherein the photobleachable dye is selected from the group consisting of xanthene dyes and fluorone dyes.

22. The method according to claim 12 wherein the photobleachable dye is selected from the group consisting of Rose Bengal, Methylene Violet, Methylene Blue, Fluorescein, Eosin Yellow, Eosin Y, Ethyl Eosin, Eosin bluish, Eosin B, Erythrosin B, Erythosin Yellowish Blend, Toluidine Blue, 4',5'-Dibromofluorescein, and blends thereof.

23. The method according to claim 12 wherein the final color is a tooth-like color.

24. The method according to claim 12 wherein the final color is able to transmit the color of an underlying surface.

25. The method according to claim 12 wherein the dental sealant undergoes a change in color, $\Delta E^*$, of greater than about 10.

26. The method according to claim 12 wherein the dental sealant undergoes a change in color, $\Delta E^*$, of greater than about 15.

27. The method according to claim 12 wherein the dental sealant undergoes a change in color, $\Delta E^*$, of greater than about 20.

28. The method according to claim 12 further comprising layering a clear coating over the dental sealant.

29. A kit comprising:

an aesthetic dental sealant comprising a hardenable resin, a hardener, and a photobleachable dye, wherein the hardener comprises a sensitizing compound different from the photobleachable dye, and wherein the dental sealant has an initial color prior to exposure to actinic radiation and a final color that is different from the initial color subsequent to the dental sealant being exposed to actinic radiation; and instructions for using the dental sealant.

30. The kit according to claim 29 further comprising an etching composition.

31. The kit according to claim 29 further comprising a priming composition.

* * * * *

UNITED STATES PATENT AND TRADEMARK OFFICE
CERTIFICATE OF CORRECTION

PATENT NO. : 6,444,725 B1
DATED : September 3, 2002
INVENTOR(S) : Trom, Matthew C.

It is certified that error appears in the above-identified patent and that said Letters Patent is hereby corrected as shown below:

Column 3,
Line 48, delete "and" and insert in place thereof -- in --.

Column 4,
Line 5, delete "SB" and insert in place thereof -- 5B --.
Line 14, delete "SB" and insert in place thereof -- 5B --.

Column 5,
Line 48, delete "blend" and insert in place thereof -- blends --.

Column 6,
Line 51, delete "-".

Column 7,
Line 36, delete "ajulolidinyl" and insert in place thereof -- a julolidinyl --.

Column 8,
Line 6, delete "2,3 –" and insert in place thereof -- 2,3- --.
Line 8, delete "2,2'-3 3'-" and insert in place thereof -- 2,2'-, 3,3'- --.

Column 9,
Line 1, delete "phenylpropan" and insert in place thereof -- phenylpropane --.
Line 4, delete "cyclopentadien" and insert in place thereof -- cyclopentadiene --.
Line 39, delete "0" and insert in place thereof -- O --.
Line 47, delete "1,1 0-" and insert in place thereof -- 1,10- --.

Column 10,
Line 63, delete "composition" and insert in place thereof -- compositions --.

Column 11,
Line 1, delete "Preferable" and insert in place thereof -- preferably --.
Line 16, delete "." following "layer".

Column 12,
Line 50, insert missing subheading -- Sample C --.

UNITED STATES PATENT AND TRADEMARK OFFICE
CERTIFICATE OF CORRECTION

PATENT NO.   : 6,444,725 B1
DATED        : September 3, 2002
INVENTOR(S)  : Trom, Matthew C.

It is certified that error appears in the above-identified patent and that said Letters Patent is hereby corrected as shown below:

Column 16,
Line 26, delete "Erythosin" and insert in place thereof -- Erythrosin --.

Signed and Sealed this

Eleventh Day of November, 2003

JAMES E. ROGAN
*Director of the United States Patent and Trademark Office*